United States Patent
Tanaka et al.

(10) Patent No.: US 10,433,605 B2
(45) Date of Patent: Oct. 8, 2019

(54) ACRYLIC FIBER FOR ARTIFICIAL HAIR, MANUFACTURING METHOD THEREFOR AND HEAD ACCESSORY CONTAINING SAME

(71) Applicant: Kaneka Corporation, Osaka (JP)

(72) Inventors: Takeshi Tanaka, Hyogo (JP); Akihiro Okamoto, Hyogo (JP); Tomomichi Hashimoto, Hyogo (JP); Sota Okumura, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 15/851,022

(22) Filed: Dec. 21, 2017

(65) Prior Publication Data

US 2018/0116322 A1    May 3, 2018

Related U.S. Application Data

(63) Continuation of application No. PCT/JP2016/068683, filed on Jun. 23, 2016.

(30) Foreign Application Priority Data

Jun. 26, 2015    (JP) ................. 2015-129190

(51) Int. Cl.
| | |
|---|---|
| *A41G 3/00* | (2006.01) |
| *A61L 27/00* | (2006.01) |
| *D01F 6/40* | (2006.01) |
| *D01F 6/10* | (2006.01) |
| *D01F 6/38* | (2006.01) |
| *D01F 11/06* | (2006.01) |
| *A41G 5/00* | (2006.01) |

(52) U.S. Cl.
CPC ............ *A41G 3/0083* (2013.01); *A61L 27/00* (2013.01); *D01F 6/10* (2013.01); *D01F 6/38* (2013.01); *D01F 6/40* (2013.01); *D01F 11/06* (2013.01); *A41G 3/0091* (2013.01); *A41G 5/008* (2013.01); *A41G 5/0046* (2013.01)

(58) Field of Classification Search
None
See application file for complete search history.

(56) References Cited

U.S. PATENT DOCUMENTS

| | | | |
|---|---|---|---|
| 2,723,900 A | 11/1955 | Hooper | |
| 3,324,215 A | 6/1967 | Rosembaum et al. | |
| T958,007 I4 | 5/1977 | Roberts | |
| 2004/0074509 A1* | 4/2004 | Murata | D01F 6/38 132/201 |
| 2007/0021543 A1* | 1/2007 | Masuda | A41G 3/0083 524/412 |
| 2007/0190322 A1 | 8/2007 | Harada | |
| 2009/0243143 A1 | 10/2009 | Zhang et al. | |
| 2009/0266372 A1 | 10/2009 | Higami et al. | |
| 2011/0120484 A1* | 5/2011 | Matsumoto | A41G 3/0083 132/53 |
| 2011/0196091 A1 | 8/2011 | Zhang et al. | |
| 2011/0271976 A1 | 11/2011 | Sasayama | |
| 2014/0109924 A1 | 4/2014 | Horihata | |

FOREIGN PATENT DOCUMENTS

| | | |
|---|---|---|
| EP | 1367153 A1 | 12/2003 |
| EP | 2123805 A1 | 11/2009 |
| EP | 2329733 A1 | 6/2011 |
| EP | 3222760 A1 | 9/2017 |
| EP | 3315038 A1 | 5/2018 |
| GB | 1308728 A | 3/1973 |
| JP | H04-245972 A | 9/1992 |
| JP | H04-263637 A | 9/1992 |
| JP | H06-073609 A | 3/1994 |
| JP | 2000-119972 A | 4/2000 |
| JP | 2002-227018 A | 8/2002 |
| JP | 2002-227028 A | 8/2002 |
| JP | 2002-249914 A | 9/2002 |
| JP | 2002-315765 A | 10/2002 |
| JP | 2003-328222 A | 11/2003 |
| JP | 2008-75210 A | 4/2008 |
| JP | 4128024 B2 | 7/2008 |
| JP | 4191930 B2 | 12/2008 |
| JP | 4203096 B2 | 12/2008 |
| JP | 2009-138314 A | 6/2009 |
| JP | 2010-512469 A | 4/2010 |
| JP | 2011-252251 A | 12/2011 |
| JP | 2012-111855 A | 6/2012 |
| JP | 5105871 B2 | 12/2012 |
| JP | 5122133 B2 | 1/2013 |
| JP | 5176960 B2 | 4/2013 |
| JP | 5492779 B2 | 5/2014 |
| JP | 2015-067925 A | 4/2015 |
| WO | 2012/043348 A1 | 4/2012 |
| WO | 2012/157561 A1 | 11/2012 |

OTHER PUBLICATIONS

International Search Report issued in International Application No. PCT/JP2016/068683; dated Sep. 20, 2016 (2 pages).
International Search Report issued in International Application No. PCT/JP2016/059669; dated Jun. 21, 2016 (2 pages).
Extended European Search Report issued in European Application No. 16772654.6, dated Oct. 18, 2018 (8 pages).

* cited by examiner

*Primary Examiner* — Brian Gulledge
(74) *Attorney, Agent, or Firm* — Osha Liang LLP

(57) ABSTRACT

An acrylic fiber for artificial hair includes an acrylic polymer, wherein the acrylic polymer includes 29.5 to 79.5% by mass of acrylonitrile, 20 to 70% by mass of vinyl chloride and/or vinylidene chloride, and 0.5 to 5% by mass of a vinyl monomer comprising a sulfonic acid group. The acrylic fiber for artificial hair includes 0.3 to 2% by mass of a good solvent for the acrylic polymer and 0.1 to 5% by mass of a compound comprising an epoxy group.

20 Claims, No Drawings

ACRYLIC FIBER FOR ARTIFICIAL HAIR, MANUFACTURING METHOD THEREFOR AND HEAD ACCESSORY CONTAINING SAME

TECHNICAL FIELD

One or more embodiments of the present invention relate to acrylic fibers for artificial hair that include an acrylic polymer formed by copolymerizing acrylonitrile and vinyl chloride and/or vinylidene chloride, that have good curl setting properties with hot water, and that reduce the generation of odorous components during heating. One or more embodiments of the present invention also relate to a method for producing the acrylic fibers for artificial hair, and hair ornament products including the acrylic fibers for artificial hair.

BACKGROUND

Conventionally, acrylic fibers have been used as fibers for artificial hair because their texture, gloss, and voluminousness are quite similar to those of human hair. For example, Patent Document 1 proposes artificial hair that uses fibers composed of an acrylic polymer containing 35 to 75% by mass of acrylonitrile, 25 to 65% by mass of a halogen-containing vinyl monomer such as vinyl chloride, and 0 to 10% by mass of a vinyl monomer copolymerizable with the acrylonitrile and the halogen-containing vinyl monomer. Patent Document 2 proposes artificial hair that uses fibers composed of an acrylic polymer containing 35 to 75% by mass of acrylonitrile, 25 to 65% by mass of vinyl chloride and/or vinylidene chloride, and 0 to 10% by mass of a vinyl monomer copolymerizable with the acrylonitrile and the vinyl chloride and/or the vinylidene chloride. Patent Document 3 proposes synthetic fibers for artificial hair that are composed of an acrylic polymer containing 30 to 80% by mass of acrylonitrile and 20 to 70% by mass of vinyl chloride and/or vinylidene chloride.

PATENT DOCUMENTS

Patent Document 1: JP 2002-227018 A
Patent Document 2: JP 2002-227028 A
Patent Document 3: WO 2012/043348

However, when acrylic fibers are produced by wet spinning the acrylic polymer that is formed by copolymerizing acrylonitrile and vinyl chloride and/or vinylidene chloride, as disclosed in Patent Documents 1 to 3, particularly by wet spinning a spinning solution in which the acrylic polymer is dissolved in dimethyl sulfoxide, such acrylic fibers have poor curl setting properties with hot water.

Moreover, when the spinning solution obtained by dissolving the acrylic polymer in dimethyl sulfoxide is used for wet spinning, the dimethyl sulfoxide may remain in the resulting fibers. Therefore, if these fibers are curled with hot water or an iron, or crimped with a gear crimper, the fibers are heated so that the dimethyl sulfoxide within the fibers is decomposed to generate malodorous components such as dimethyl sulfide and dimethyl disulfide.

SUMMARY

One or more embodiments of the present invention provide acrylic fibers for artificial hair that include an acrylic polymer formed by copolymerizing acrylonitrile and vinyl chloride and/or vinylidene chloride, that have good curl setting properties with hot water, and that reduce the generation of malodorous components during heating. One or more embodiments of the present invention also provide a method for producing the acrylic fibers for artificial hair, and hair ornament products including the acrylic fibers for artificial hair.

One or more embodiments of the present invention relate to an acrylic fiber for artificial hair that includes an acrylic polymer. The acrylic polymer contains 29.5 to 79.5% by mass of acrylonitrile, 20 to 70% by mass of vinyl chloride and/or vinylidene chloride, and 0.5 to 5% by mass of a sulfonic acid group-containing vinyl monomer with respect to a total mass of the acrylic polymer. The acrylic fiber for artificial hair includes 0.3 to 2% by mass of a good solvent for the acrylic polymer and 0.1 to 5% by mass of an epoxy group-containing compound.

One or more embodiments of the present invention also relate to a method for producing an acrylic fiber for artificial hair that includes an acrylic polymer. The acrylic polymer contains 29.5 to 79.5% by mass of acrylonitrile, 20 to 70% by mass of vinyl chloride and/or vinylidene chloride, and 0.5 to 5% by mass of a sulfonic acid group-containing vinyl monomer. The method includes: preparing a spinning solution that contains the acrylic polymer, an epoxy group-containing compound, and a good solvent for the acrylic polymer; and wet spinning the spinning solution to form an acrylic fiber in which a content of the good solvent for the acrylic polymer is 0.3 to 2% by mass and a content of the epoxy group-containing compound is 0.1 to 5% by mass.

One or more embodiments of the present invention also relate to a hair ornament product including the acrylic fiber for artificial hair.

One or more embodiments of the present invention can provide acrylic fibers for artificial hair that include an acrylic polymer formed by copolymerizing acrylonitrile and vinyl chloride and/or vinylidene chloride, that have good curl setting properties with hot water, and that reduce the generation of malodorous components during heating. One or more embodiments of the present invention can also provide hair ornament products including the acrylic fibers for artificial hair.

The production method according to one or more embodiments of the present invention can provide acrylic fibers for artificial hair that include an acrylic polymer formed by copolymerizing acrylonitrile and vinyl chloride and/or vinylidene chloride, that have good curl setting properties with hot water, and that reduce the generation of malodorous components during heating.

DETAILED DESCRIPTION OF EMBODIMENTS

The present inventors conducted intensive studies to improve the curl setting properties of acrylic fibers with hot water. The acrylic fibers included an acrylic polymer formed by copolymerizing acrylonitrile, vinyl chloride and/or vinylidene chloride, and a sulfonic acid-containing vinyl monomer. As a result, the present inventors surprisingly found that the acrylic fibers had improved curl setting properties with hot water by intentionally incorporating a predetermined amount of a good solvent for the acrylic polymer. Moreover, the present inventors also found that the acrylic fibers including a predetermined amount of an epoxy group-containing compound was able to reduce the generation of malodorous components such as dimethyl sulfide and dimethyl disulfide in a drying process or a heat-treatment process, even though the acrylic fibers included a sulfur-containing solvent such as dimethyl sulfoxide as a good solvent for the acrylic polymer. Based on these findings, the present inventors have reached one or more embodiments of the present invention. In general, the epoxy group-containing compound may be used as a flame retardant in synthetic fibers. Surprisingly, when the epoxy group-containing compound is used in the acrylic fibers including a sulfur-containing solvent such as dimethyl sulfoxide, it can suppress the decomposition of the sulfur-containing solvent caused by heating of the acrylic fibers. The mechanism for suppressing the decomposition of the sulfur-containing solvent such as dimethyl sulfoxide in the presence of the epoxy group-containing compound is still unclear, but can be estimated as follows. When the acrylic fibers are heated, a dehydrochlorination reaction of the acrylic polymer in the acrylic fibers occurs, so that the sulfur-containing solvent is decomposed by the hydrochloric acid produced. The epoxy group-containing compound traps the hydrochloric acid, and thus can suppress the decomposition of the sulfur-containing solvent such as dimethyl sulfoxide or dimethyl disulfide.

The acrylic polymer contains 29.5 to 79.5% by mass of acrylonitrile, 20 to 70% by mass of vinyl chloride and/or vinylidene chloride, and 0.5 to 5% by mass of a sulfonic acid group-containing vinyl monomer with respect to the total mass of the acrylic polymer. In other words, the acrylic polymer is obtained by polymerizing a total of 100% by mass of a monomer mixture containing 29.5 to 79.5% by mass of acrylonitrile, 20 to 70% by mass of vinyl chloride and/or vinylidene chloride, and 0.5 to 5% by mass of a sulfonic acid group-containing vinyl monomer. When the content of acrylonitrile in the acrylic polymer is 29.5 to 79.5% by mass, the heat resistance is improved. When the content of vinyl chloride and/or vinylidene chloride in the acrylic polymer is 20 to 70% by mass, the flame resistance is improved. When the acrylic polymer contains 0.5 to 5% by mass of a sulfonic acid group-containing vinyl monomer, the hydrophilicity is increased. The acrylic polymer may contain 34.5 to 74.5% by mass of acrylonitrile, 25 to 65% by mass of vinyl chloride and/or vinylidene chloride, and 0.5 to 5% by mass of a sulfonic acid group-containing vinyl monomer with respect to the total mass of the acrylic polymer. The acrylic polymer may contain 39.5 to 74.5% by mass of acrylonitrile, 25 to 60% by mass of vinyl chloride, and 0.5 to 5% by mass of a sulfonic acid group-containing vinyl monomer with respect to the total mass of the acrylic polymer. The acrylic polymer may contain vinyl chloride from the viewpoint of excellent texture.

The sulfonic acid group-containing vinyl monomer is not particularly limited. Examples of the sulfonic acid group-containing vinyl monomer include allylsulfonic acid, methallylsulfonic acid, styrenesulfonic acid, isoprenesulfonic acid, 2-acrylamido-2-methylpropanesulfonic acid, and metal salts such as sodium salts thereof and amine salts thereof. These sulfonic acid group-containing vinyl monomers may be used individually or in combination of two or more.

In the acrylic fibers for artificial hair, the content of the good solvent for the acrylic polymer (also referred to as a "solvent A" in the following) is 0.3 to 2% by mass. When the content of the solvent A in the acrylic fibers is within the above range, both the curl setting properties with hot water and the spinnability are improved. On the other hand, if the content of the solvent A in the acrylic fibers is less than 0.3% by mass, it is difficult to improve the curl setting properties with hot water. If the content of the solvent A in the acrylic fibers is more than 2% by mass, the curl retention properties may be degraded, and a single yarn breakage may occur due to poor spinnability. The content of the solvent A in the acrylic fibers may be 0.4% by mass or more, 0.5% by mass or more, or 0.6% by mass or more. In this case, the content of the solvent A in the acrylic fibers may be 1.5% by mass or less, 1.2% by mass or less, or 1.0% by mass or less. In one or more embodiments of the present invention, the good solvent for the acrylic polymer means a solvent that can dissolve the acrylic polymer and has a boiling point of 60° C. or more. For example, the solvent A may be at least one selected from the group consisting of dimethyl sulfoxide, N,N-dimethylformamide, dimethylacetamide, dimethyl sulfone, ε-caprolactam, ethylene carbonate, and sulfolane. From the viewpoint of safety for the human body, the solvent A may be at least one selected from the group consisting of dimethyl sulfoxide, dimethyl sulfone, ε-caprolactam, ethylene carbonate, and sulfolane, and may be at least one selected from the group consisting of dimethyl sulfoxide and dimethyl sulfone. In one or more embodiments of the present invention, when the acrylic fibers for artificial hair include two or more types of solvents A, the content of the solvents A represents the total content of the two or more types of solvents A. In one or more embodiments of the present invention, the solvent A has the function of improving the curl setting properties of the acrylic fibers with hot water. Therefore, the content of the solvent A in the fibers may be 0.3 to 2% by mass before heat setting or the like. The content of the solvent A in the fibers may be either 0.3 to 2% by mass or less than 0.3% by mass after heat setting or the like.

In one or more embodiments of the present invention, the content of the solvent A in the acrylic fibers is measured and calculated as follows. A glass sample bottle containing pure water is prepared, in which fibers are placed so that the water will not overflow. After the glass sample bottle is sealed, the fibers are heated in hot water at 95° C. or more for 2 hours or more to extract the solvent A in the fibers. Subsequently, the glass sample bottle is cooled to room temperature. The extract, which has been cooled to room temperature, is analyzed by, e.g., gas chromatography, and the mass (W1) of the solvent A in the fibers is calculated. The fibers in the glass sample bottle are washed with pure water, and then dried at 110° C. for 4 hours or more. Thus, the mass (W2) of the dried fibers is measured. Using the following formula, the content of the solvent A in the acrylic fibers is calculated.

Content of solvent $A$ in acrylic fiber (% by mass)= $(W1)/(W1+W2) \times 100$

The acrylic fibers for artificial hair include 0.1 to 5% by mass of the epoxy group-containing compound. This can improve the curl setting properties with hot water and reduce the generation of malodorous components during heating. From the viewpoint of reducing the generation of malodorous components more effectively when the acrylic fibers are heated, the acrylic fibers may include 0.2% by mass or more or 0.3% by mass or more of the epoxy group-containing compound. From the viewpoint of spinnability, fiber quality, and cost, the acrylic fibers may include 3% by mass or less or 1.5% by mass or less of the epoxy group-containing compound.

In one or more embodiments of the present invention, the content of the epoxy group-containing compound in the acrylic fibers is measured and calculated as follows. First, 1 g of a fiber sample is dissolved in 10 g of acetone, and then 90 g of methoxypropanol is added to precipitate only an acrylic polymer. The mixed solvent of acetone and methoxypropanol that dissolves the fiber sample is sampled, which is then dried and solidified at 120° C. with a vacuum dryer. The infrared absorption analysis of the compound thus obtained confirms that there is a peak corresponding to the presence of an oxirane ring. Based on the ratio of the extracted amount of the compound and the mass of the fibers, the content of the epoxy group-containing compound in the fibers is calculated.

Examples of the epoxy group-containing compound include a glycidyl methacrylate-containing polymer, a glycidyl acrylate-containing polymer, an epoxidized vegetable oil, a glycidyl ether type epoxy resin, a glycidyl amine type epoxy resin, a glycidyl ester type epoxy resin, and a cyclic aliphatic type epoxy resin. These epoxy group-containing compounds may be used individually or in combination of two or more.

The glycidyl methacrylate-containing polymer is not particularly limited. Examples of the glycidyl methacrylate-containing polymer include polyglycidyl methacrylate, and copolymers obtained by copolymerizing glycidyl methacrylate and other monomers that are copolymerizable with the glycidyl methacrylate. Examples of the glycidyl acrylate-containing polymer include polyglycidyl acrylate, and copolymers obtained by copolymerizing glycidyl acrylate and other monomers that are copolymerizable with the glycidyl acrylate. The copolymers obtained by copolymerizing glycidyl methacrylate and other monomers that are copolymerizable with the glycidyl methacrylate may include, e.g., a copolymer of glycidyl methacrylate and styrene and a copolymer of glycidyl methacrylate and methyl methacrylate.

The epoxidized vegetable oil is not particularly limited, and may be, e.g., epoxidized soybean oil or epoxidized linseed oil.

The glycidyl ether type epoxy resin is not particularly limited, and may be, e.g., a bisphenol A type epoxy resin, a bisphenol F type epoxy resin, a brominated bisphenol A type epoxy resin, a hydrogenated bisphenol A type epoxy resin, a biphenyl type epoxy resin, a naphthalene type epoxy resin, a phenolic novolac type epoxy resin, an ortho-cresol novolac type epoxy resin, a bisphenol A novolac type epoxy resin, a trishydroxymethane type epoxy resin, or a tetraphenolethane type epoxy resin.

The glycidyl amine type epoxy resin is not particularly limited, and may be, e.g., tetraglycidyl diaminodiphenyl methane, triglycidyl isocyanurate, an aminophenol type epoxy resin, or an aniline type epoxy resin.

The glycidyl ester type epoxy resin is not particularly limited, and may be, e.g., a hexahydrophthalic anhydride type epoxy resin or a dimer acid type epoxy resin.

The cyclic aliphatic type epoxy resin is not particularly limited, and may be, e.g., an alicyclic acetal type epoxy resin, an alicyclic adipate type epoxy resin, an alicyclic carboxylate type epoxy resin, or a vinylcyclohexene type epoxy resin.

From the viewpoint of epoxy equivalent (i.e., the mass of the resin containing 1 equivalent of epoxy group), suppressing the coloring of the fibers, the solubility in dimethyl sulfoxide, and reducing the elution into a spinning bath, the epoxy group-containing compound may be a glycidyl methacrylate-containing polymer and/or a glycidyl acrylate-containing polymer, or polyglycidyl methacrylate. From the viewpoint of increasing the heat resistance, the epoxy group-containing compound may be a copolymer of glycidyl methacrylate and styrene.

The mass average molecular weight of the epoxy group-containing compound may be appropriately determined in view of the solubility in dimethyl sulfoxide and the elution into the spinning bath. When the epoxy group-containing compound is a glycidyl methacrylate-containing polymer and/or a glycidyl acrylate-containing polymer, e.g., the mass average molecular weight may be 3000 or more from the viewpoint of reducing the elution into the spinning bath, and the mass average molecular weight may be 100000 or less from the viewpoint of the solubility in dimethyl sulfoxide.

The acrylic fibers for artificial hair may have an apparent glass transition temperature (apparent Tg) of 89° C. or less, 88° C. or less, or 87° C. or less. When the apparent Tg of the fibers is within the above range, the curl setting properties with hot water can be improved, even if the temperature of the hot water is low, e.g., at 60 to 70° C. In one or more embodiments of the present invention, the apparent Tg of the fibers means a peak temperature of tan δ. The peak temperature of tan δ is a temperature at which dynamic viscoelasticity (tan δ) reaches the maximum value. The dynamic viscoelasticity (tan δ) is calculated by the following formula:

$$\text{Dynamic viscoelasticity}(\tan \delta) = \text{Loss modulus}(E")/\text{Storage modulus}(E'),$$

where the loss modulus (E") and the storage modulus (E') of the fibers are measured in accordance with JIS K 7244 by a thermal analysis measuring device.

When 0.02 g of the acrylic fibers are placed in a 20 mL vial and heated at 140° C. for 5 minutes, the concentration of dimethyl sulfide generated in the vial may be 25 ppm or less and the concentration of dimethyl disulfide generated in the vial may be 5 ppm or less. The acrylic fibers satisfying these conditions emit almost no foul odor even if they are heated at a predetermined temperature, e.g., in the curling process with hot water at 70° C. or more, in the curling process using a hair iron at 100° C. or more, or in the crimping process using a gear crimper at 100° C. or more. The concentration of the dimethyl sulfide may be 25 ppm or less and the concentration of the dimethyl disulfide may be 1 ppm or less. The concentration of the dimethyl sulfide may be 1 ppm or less and the concentration of the dimethyl disulfide may be 1 ppm or less.

The acrylic fibers for artificial hair are cut to a length of 450 mm, and the resulting fiber bundle (with a total fineness of 4600 dtex) is wound around a 15 mm diameter pipe (metal cylinder) and fixed. This fiber bundle is immersed in hot water at 80° C. for 15 seconds, and then dried by ventilation drying at room temperature (25±5° C.) and a relative humidity of 50% for 8 hours. Subsequently, the fiber bundle is removed from the pipe. The length of the fiber bundle that is hanged immediately after removal from the pipe may be 175 mm or less. This leads to better curl setting properties with hot water. The length of the fiber bundle may be 172 mm or less, or 170 mm or less.

A method for producing the acrylic fibers for artificial hair is not particularly limited, and may include the following: preparing a spinning solution by dissolving the acrylic polymer in the solvent A such as dimethyl sulfoxide, and adding the epoxy group-containing compound to the acrylic polymer solution; and wet spinning the spinning solution. In this case, the acrylic fibers may be produced (i) by adjusting the degree of water washing so that the content of the solvent A (e.g., dimethyl sulfoxide) used for the spinning solution is 0.3 to 2.0% by mass, and/or (ii) by impregnating a water-washed primary drawn yarn with a solvent A that is the same as or different from the solvent A used for the spinning solution so that the content (total content) of the solvent A in the acrylic fibers is 0.3 to 2.0% by mass.

Although depending on the composition of the acrylic polymer, the spinning solution may contain, e.g., 20 to 30% by mass of the acrylic polymer, 22 to 30% by mass of the acrylic polymer, or 25 to 30% by mass of the acrylic polymer with respect to the total mass of the spinning solution.

The spinning solution may contain 0.1 to 5 parts by mass of the epoxy group-containing compound with respect to 100 parts by mass of the acrylic polymer so as to make it easy to provide fibers in which the content of the epoxy group-containing compound is 0.1 to 5% by mass. The spinning solution may contain 0.2 to 3 parts by mass of the epoxy group-containing compound, or 0.3 to 1 parts by mass of the epoxy group-containing compound with respect to 100 parts by mass of the acrylic polymer. The epoxy group-containing compound may be any of those described above. Although depending on the type of the epoxy group-containing compound, if the spinning solution contains more than 5 parts by mass of the epoxy group-containing compound with respect to 100 parts by mass of the acrylic polymer, there is concern that the spinning solution may be thickened and the spinnability may be degraded. Moreover, since a part of the epoxy group is ring-opened and cross-linked in the drying process and the drawing process, there is also concern that the extensibility of the fibers may be reduced, resulting in poor spinnability such as a single yarn breakage.

The spinning solution may further contain inorganic polyphosphate. This can prevent the coloring of the acrylic fibers. From the viewpoint of color protection and spinnability, the spinning solution may contain 0.01 to 5 parts by mass of the inorganic polyphosphate, 0.015 to 4 parts by mass of the inorganic polyphosphate, or 0.03 to 2 parts by mass of the inorganic polyphosphate with respect to 100 parts by mass of the acrylic polymer. From the viewpoint of ease of handling, an aqueous solution of the inorganic polyphosphate may be added to the spinning solution.

The spinning solution may also contain other additives as needed to modify the fiber characteristics. Examples of the additives include gloss control agents such as titanium dioxide, silicon dioxide, and esters and ethers of cellulose derivatives including cellulose acetate, coloring agents such as organic pigments, inorganic pigments, and dyes, and stabilizers for improving light resistance and heat resistance.

The wet spinning includes at least a coagulation process, a water washing process, and a drying process. The wet spinning may include a bath drawing process that is to be performed before or after the water washing process. Moreover, the wet spinning may include an oil application process that is to be performed before the drying process. Further, the wet spinning may include a drawing process and a thermal relaxation process that are to be performed after the drying process.

First, the spinning solution is extruded through a spinning nozzle into a coagulation solution (coagulation bath) containing an aqueous solution of the solvent A used for the spinning solution, where the extruded spinning solution is coagulated to form filaments (undrawn filaments). The coagulation bath may contain an aqueous solution of the solvent A used for the spinning solution such as dimethyl sulfoxide with a concentration of 40 to 70% by mass. The temperature of the coagulation bath may be 5 to 40° C. If the solvent concentration in the coagulation bath is too low, the coagulation is accelerated, and thus it is likely that a coagulation structure will be rough and voids will be formed inside the fibers.

Next, in the bath drawing process, the acrylic fibers (also referred to as "coagulated yarns") may be drawn in a drawing bath (also referred to as "primary drawing"). The drawing bath may be a water bath or may contain an aqueous solution of the solvent A having a lower concentration than that of the coagulation bath. The temperature of the drawing bath may be 30° C. or more, 40° C. or more, or 50° C. or more. The draw ratio is not particularly limited, and may be 2 to 8 times, 2 to 7 times, or 2 to 6 times from the viewpoint of improving the fiber strength and the productivity. When the primary drawing uses a water bath, the bath drawing process may be performed after the water washing process, as will be described later, or the primary drawing and water washing may be performed simultaneously.

Next, in the water washing process, the acrylic fibers are washed with warm water at 30° C. or more to remove the solvent A from the acrylic fibers. Alternatively, the coagulated yarns are introduced into warm water at 30° C. or more, and subjected to the primary drawing together with water washing. In the water washing process, the content of the solvent A in the acrylic fibers can be adjusted to 0.3 to 2.0% by mass by controlling the temperature of the warm water without removing the solvent A completely.

Another method may be used to adjust the content of the solvent A in the acrylic fibers to 0.3 to 2.0% by mass. In this method, part or almost all of the solvent A is removed from the acrylic fibers in the water washing process, and then the washed acrylic fibers are further impregnated with the solvent A. The solvent A can be removed substantially completely from the acrylic fibers by using warm water at 90° C. or more in the water washing process. Next, the water-washed primary drawn yarn is impregnated with the solvent A. In this case, the fibers have been swelled by water washing, and therefore are easily impregnated with the solvent A. From the viewpoint of facilitating the impregnation of the fibers with the solvent A, the molecular weight of the solvent A may be 300 or less, or 100 or less. From the viewpoint of preventing the evaporation of the solvent A in the drying process, the boiling point of the solvent A may be higher than that of water. From the viewpoint of a high boiling point and a low molecular weight, the solvent A may be at least one selected from the group consisting of dimethyl sulfoxide, N,N-dimethylformamide, dimethylacetamide, dimethyl sulfone, ε-caprolactam, ethylene carbonate, and sulfolane. The solvent A may be at least one selected from the group consisting of dimethyl sulfoxide, dimethyl sulfone, ε-caprolactam, ethylene carbonate, and sulfolane.

From the viewpoint of simplification of the operation and ease of adjustment of the degree of impregnation with the organic solvent, the water-washed primary drawn yarn may be impregnated with a mixture of the solvent A and an oil. In other words, the impregnation of the primary drawn yarn with the solvent A may be performed at the same time as the application of the oil to the primary drawn yarn. The impregnation is not particularly limited, and may be performed, e.g., by spraying the mixture of the solvent A and the oil onto the water-washed primary drawn yarn, or by immersing the water-washed primary drawn yarn in the mixture of the solvent A and the oil. The content of the solvent A in the acrylic fibers can be adjusted by appropriately selecting the impregnation method or the mixing ratio of the solvent A in the mixture of the solvent A and the oil. When there is no need to further impregnate the acrylic fibers with the solvent A because a predetermined amount of the solvent A is left in the acrylic fibers in the water washing process, only the oil may be applied to the acrylic fibers in the usual manner in the oil application process.

The oil may be generally used to prevent static electricity, to prevent the adhesion between fibers, or to improve the texture in the production of the fibers. Any known oil can be used for these purposes. Examples of such oil include the following: anionic surfactants such as phosphates and sulfates; cationic surfactants such as quaternary ammonium salts and imidazolium salts; nonionic surfactants such as ethylene oxide adducts and/or propylene oxide adducts of fats and oils, and polyhydric alcohol partial esters; animal and vegetable fats and oils, mineral oils, and fatty acid esters; and silicone-based surfactants such as amino-modified silicones. These oils may be used individually or in combination of two or more. From the viewpoint of the stability of oil particles and the adjustment of the optimum solvent content by mixing the good solvent with the oil, the mixture of the good solvent and the oil may contain 0.1 to 10 parts by mass of the good solvent, 0.2 to 5 parts by mass of the good solvent, or 0.3 to 2 parts by mass of the good solvent with respect to 100 parts by mass of the oil. In this case, the oil may also be an oil solution that is a mixed solution of the oil and water.

Next, in the drying process, the acrylic fibers to which the oil has been applied are dried. The drying temperature is not particularly limited, and may be, e.g., 110 to 190° C., or 110 to 160° C. Then, the dried fibers may further be drawn as needed (secondary drawing). The drawing temperature of the secondary drawing is not particularly limited, and may be, e.g., 110 to 190° C., or 110 to 160° C. The draw ratio is not particularly limited, and may be, e.g., 1 to 4 times. The total draw ratio, including the bath drawing before the drying process, may be 2 to 12 times.

The fibers that have been dried or that have been dried and then drawn may be relaxed in the thermal relaxation process. The relaxation rate is not particularly limited, and may be, e.g., 5% or more, or 10% or more. The thermal relaxation treatment can be performed in a dry heat atmosphere or a superheated steam atmosphere at a high temperature, e.g., at 150 to 200° C., or at 150 to 190° C. Alternatively, the thermal relaxation treatment can be performed in a pressurized steam atmosphere or a heated and pressurized steam atmosphere at 120 to 180° C. under 0.05 to 0.4 MPa, or under 0.1 to 0.4 MPa.

The single fiber fineness of the acrylic fibers for artificial hair may be 10 to 100 dtex, 20 to 95 dtex, 30 to 90 dtex, 40 to 80 dtex, or 45 to 70 dtex from the viewpoint of making the fibers suitable for artificial hair. In this specification, the single fiber fineness means the average fineness of 100 randomly selected filaments.

The acrylic fibers for artificial hair have good curl setting properties with hot water (also simply referred to as "HWS properties" in the following). For example, the acrylic fibers can be curled in hot water at 60 to 100° C. The curling method is not particularly limited, and may be appropriately selected in accordance with the purpose and the intended use. Examples of the curling method include twisting, pipe winding (i.e., winding fibers around a metal cylinder), and net processing (YAKI processing).

The acrylic fibers for artificial hair can be used to produce hair ornament products. The hair ornament products may include other fibers for artificial hair in addition to the above acrylic fibers. The other fibers for artificial hair are not particularly limited, and may be, e.g., polyvinyl chloride fibers, nylon fibers, polyester fibers, or regenerated collagen fibers.

The hair ornament products may include, e.g., fiber bundles for hair, hair weaves, wigs, braids, toupee, hair extensions, and hair accessories.

EXAMPLES

Hereinafter, one or more embodiments of the present invention will be described by way of examples. However, the present invention is not limited to the following examples.

Example 1

An acrylic polymer containing 46% by mass of acrylonitrile, 52% by mass of vinyl chloride, and 2% by mass of sodium styrenesulfonate was dissolved in dimethyl sulfoxide to form a solution having a resin concentration of 28.0% by mass. Next, an aqueous solution of sodium tripolyphosphate with a concentration of 1.22% by mass was added to this solution so that the content of the sodium tripolyphosphate was 3.5 parts by mass with respect to 100 parts by mass of the acrylic polymer. Moreover, polyglycidyl methacrylate (mass average molecular weight: 12000) was added to the solution in an amount of 1.0 part by mass with respect to 100 parts by mass of the acrylic polymer, thereby preparing a spinning solution. The spinning solution was extruded through a spinning nozzle (pore diameter: 0.3 mm, the number of pores: 100) into a coagulation bath containing an aqueous solution of dimethyl sulfoxide with a concentration of 62% by mass at 20° C., where the extruded spinning solution was coagulated to form filaments. Then, the filaments were drawn to three times their original length in a drawing bath containing an aqueous solution of dimethyl sulfoxide with a concentration of 50% by mass at 80° C. Subsequently, the drawn yarns were washed with warm water at 90° C. Next, the water-washed primary drawn yarns were immersed in an oil bath (60° C.) for 1 to 3 seconds. The oil bath contained a mixture of oil (including a fatty acid ester oil and a polyoxyethylene surfactant) and dimethyl sulfoxide. Thus, the drawn yarns were impregnated with the mixture of oil and dimethyl sulfoxide. Thereafter, the drawn yarns were dried by uniform hot air at 140° C. and a heated roll at 160° C. in sequence, and further drawn to two times at 130° C. The resulting yarns were subjected to a 20% relaxation treatment at 154° C. to provide acrylic fibers having a single fiber fineness of about 46 dtex. In the oil bath, the amount of dimethyl sulfoxide added was 2.0 parts by mass with respect to 100 parts by mass of the oil (i.e., the mixture of the fatty acid ester oil, the polyoxyethylene surfactant, and water).

Example 2

Acrylic fibers having a single fiber fineness of about 46 dtex were produced in the same manner as Example 1, except that a mixture containing 1.0 part by mass of dimethyl sulfoxide with respect to 100 parts by mass of the oil was introduced into the oil bath.

Example 3

Acrylic fibers having a single fiber fineness of about 46 dtex were produced in the same manner as Example 1, except that the drawn yarns were washed with warm water at 70° C., and only the oil (i.e., the mixture of the fatty acid ester oil, the polyoxyethylene surfactant, and water) was introduced into the oil bath.

Example 4

Acrylic fibers having a single fiber fineness of about 46 dtex were produced in the same manner as Example 3, except that the polyglycidyl methacrylate was replaced by a copolymer (mass average molecular weight: 20000) containing 49% by mass of glycidyl methacrylate and 51% by mass of styrene.

Example 5

Acrylic fibers having a single fiber fineness of about 46 dtex were produced in the same manner as Example 3, except that polyglycidyl methacrylate was added in an amount of 0.1 parts by mass with respect to 100 parts by mass of the acrylic polymer.

Example 6

Acrylic fibers having a single fiber fineness of about 46 dtex were produced in the same manner as Example 3, except that polyglycidyl methacrylate was added in an amount of 0.5 parts by mass with respect to 100 parts by mass of the acrylic polymer.

Example 7

An acrylic polymer containing 46% by mass of acrylonitrile, 52% by mass of vinyl chloride, and 2% by mass of sodium styrenesulfonate was dissolved in dimethyl sulfoxide to form a resin solution having a resin concentration of 28.0% by mass and a water concentration of 3.5% by mass. Next, coloring agents, i.e., carbon black, a red dye (C. I. Basic Red 46), and a blue dye (C. I. Basic Blue 41) were added to the resin solution in amounts of 2.1 parts by mass, 0.04 parts by mass, and 0.07 parts by mass with respect to 100 parts by mass of the acrylic polymer, respectively. Moreover, polyglycidyl methacrylate (mass average molecular weight: 12000) was added to the resin solution in an amount of 1.0 part by mass with respect to 100 parts by mass of the acrylic polymer, thereby preparing a spinning solution. The spinning solution was extruded through a spinning nozzle (pore diameter: 0.3 mm, the number of pores: 1250) into a coagulation bath containing an aqueous solution of dimethyl sulfoxide with a concentration of 62% by mass at 20° C., where the extruded spinning solution was coagulated to form filaments. Then, the filaments were drawn to three times their original length in a drawing bath containing an aqueous solution of dimethyl sulfoxide with a concentration of 50% by mass at 80° C. Subsequently, the drawn yarns were washed with warm water at 80° C. Next, the water-washed primary drawn yarns were immersed in an oil bath (60° C.) for 3 to 5 seconds. The oil bath contained a mixture of oil (including a fatty acid ester oil and a polyoxyethylene surfactant) and dimethyl sulfone. Thus, the drawn yarns were impregnated with the mixture of oil and dimethyl sulfone. Thereafter, the drawn yarns were dried at 140° C., and further drawn to two times. The resulting yarns were subjected to a 20% relaxation treatment at 160° C. to provide acrylic fibers having a single fiber fineness of about 46 dtex. In the oil bath, the amount of dimethyl sulfone added was 0.8 parts by mass with respect to 100 parts by mass of the oil (i.e., the mixture of the fatty acid ester oil, the polyoxyethylene surfactant, and water).

Example 8

Acrylic fibers having a single fiber fineness of about 46 dtex were produced in the same manner as Example 7, except that polyglycidyl methacrylate (mass average molecular weight: 12000) was added in an amount of 0.75 parts by mass with respect to 100 parts by mass of the acrylic polymer, the drawn yarns were washed with warm water at 90° C., and a mixture containing 1.1 parts by mass of dimethyl sulfone with respect to 100 parts by mass of the oil was introduced into the oil bath.

Example 9

Acrylic fibers having a single fiber fineness of about 46 dtex were produced in the same manner as Example 8, except that polyglycidyl methacrylate (mass average molecular weight: 12000) was added in an amount of 1.2 parts by mass with respect to 100 parts by mass of the acrylic polymer.

Example 10

Acrylic fibers having a single fiber fineness of about 46 dtex were produced in the same manner as Example 7, except that polyglycidyl methacrylate (mass average molecular weight: 12000) was added in an amount of 5 parts by mass with respect to 100 parts by mass of the acrylic polymer, the drawn yarns were washed with warm water at 70° C., and a mixture containing 1.5 parts by mass of dimethyl sulfone with respect to 100 parts by mass of the oil was introduced into the oil bath.

Example 11

Acrylic fibers having a single fiber fineness of about 46 dtex were produced in the same manner as Example 8, except that polyglycidyl methacrylate (mass average molecular weight: 12000) was added in an amount of 1.0 part by mass with respect to 100 parts by mass of the acrylic polymer, and a mixture containing 1.5 parts by mass of ethylene carbonate with respect to 100 parts by mass of the oil was introduced into the oil bath.

Example 12

Acrylic fibers having a single fiber fineness of about 46 dtex were produced in the same manner as Example 8, except that a mixture containing 1.5 parts by mass of sulfolane with respect to 100 parts by mass of the oil was introduced into the oil bath.

Example 13

Acrylic fibers having a single fiber fineness of about 46 dtex were produced in the same manner as Example 8, except that a copolymer (mass average molecular weight: 17000) containing glycidyl methacrylate and methyl methacrylate at a mass ratio of 70:30 was added in an amount of 1.2 parts by mass with respect to 100 parts by mass of the acrylic polymer, and a mixture containing 1.2 parts by mass of dimethyl sulfone with respect to 100 parts by mass of the oil was introduced into the oil bath.

Comparative Example 1

Acrylic fibers having a single fiber fineness of about 46 dtex were produced in the same manner as Example 1, except that polyglycidyl methacrylate was not added to the spinning solution.

Comparative Example 2

Acrylic fibers having a single fiber fineness of about 46 dtex were produced in the same manner as Comparative Example 1, except that the drawn yarns were washed with warm water at 80° C., and only the oil (i.e., the mixture of the fatty acid ester oil, the polyoxyethylene surfactant, and water) was introduced into the oil bath.

Comparative Example 3

Acrylic fibers having a single fiber fineness of about 46 dtex were produced in the same manner as Comparative Example 1, except that only the oil (i.e., the mixture of the fatty acid ester oil, the polyoxyethylene surfactant, and water) was introduced into the oil bath.

Comparative Example 4

Acrylic fibers having a single fiber fineness of about 46 dtex were produced in the same manner as Example 1, except that only the oil (i.e., the mixture of the fatty acid ester oil, the polyoxyethylene surfactant, and water) was introduced into the oil bath.

The content of the solvent A and the content of the epoxy group-containing compound in the acrylic fibers in Examples 1 to 13 and Comparative Examples 1 to 4 were measured and calculated as follows. The curl setting properties of the acrylic fibers with hot water in Examples 1 to 13 and Comparative Examples 1 to 4 were evaluated as follows. The generation of foul odor during the heating of the acrylic fibers in Examples 1 to 13 and Comparative Examples 1 to 4 was evaluated by performing a heat test in which the concentrations of the generated dimethyl sulfide and dimethyl disulfide were measured, as will be described later. Moreover, the apparent Tg (i.e., the peak temperature of tan δ) of the acrylic fibers in Examples 1 to 13 and Comparative Examples 1 to 4 was measured as follows. Table 1 shows the results.

(Content of Solvent A in Acrylic Fibers)

A glass sample bottle containing pure water was prepared, in which fibers were placed so that the water would not overflow. Then, the fibers were heated in hot water at 95° C. or more for 2 hours or more to extract the solvent A in the fibers. The extract was analyzed by, e.g., gas chromatography, and the mass (W1) of the solvent A in the fibers was calculated. The fibers in the glass sample bottle were washed with pure water, and then dried at 110° C. for 4 hours or more. Thus, the mass (W2) of the dried fibers was measured. Using the following formula, the content of the solvent A in the acrylic fibers was calculated.

Content of solvent $A$ in acrylic fiber (% by mass)= $(W1)/(W1+W2) \times 100$ (Content of Epoxy Group-Containing Compound in Acrylic Fibers)

First, 1 g of a fiber sample was dissolved in 10 g of acetone, and then 90 g of methoxypropanol was added to precipitate only an acrylic polymer. The mixed solvent of acetone and methoxypropanol that dissolved the fiber sample was sampled, which was then dried and solidified at 120° C. with a vacuum dryer. The infrared absorption analysis of the compound thus obtained confirmed that there was a peak corresponding to the presence of an oxirane ring. Based on the ratio of the extracted amount of the compound and the mass of the fibers, the content of the epoxy group-containing compound in the fibers was calculated.

(Curl Setting Properties with Hot Water)

Acrylic fibers (total fineness: 4600 dtex) were cut to a length of 450 mm, and the resulting fiber bundle was wound around a 15 mm diameter pipe and fixed. This fiber bundle was immersed in hot water at 80° C. for 15 seconds, and then dried by ventilation drying at room temperature (25±5° C.) and a relative humidity of 50% for 8 hours. Subsequently, the fiber bundle was removed from the pipe, and the length of the fiber bundle that was hanged immediately after removal from the pipe was measured. Based on the measured length of the fiber bundle, the curl setting properties (also referred to as "HWS properties" in the following) with hot water were evaluated in accordance with the following criteria.

A: The length of the fiber bundle is 175 mm or less, indicating good HWS properties.

B: The length of the fiber bundle is more than 175 mm, indicating poor HWS properties.

(Method for Evaluating Foul Odor)

0.02 g of fibers were placed in a 20 mL vial and heated at 140° C. for 5 minutes. Then, 0.2 mL of a headspace gas phase was directly introduced with a gas tight syringe, and GC/MS ("QP-2010 PLUS" manufactured by Shimadzu Corporation) was used to quantify dimethyl sulfide (also referred to as "DMS" in the following) and dimethyl disulfide (also referred to as "DMDS" in the following). Based on the concentrations of the quantified dimethyl sulfide and dimethyl disulfide, the generation of a foul odor was evaluated in accordance with the following criteria.

A: The concentration of the dimethyl sulfide is 1 ppm or less, and the concentration of the dimethyl disulfide is 1 ppm or less, so that no foul odor is generated.

B: The concentration of the dimethyl sulfide is 25 ppm or less, and the concentration of the dimethyl disulfide is 5 ppm or less, so that almost no foul odor is generated.

C: The concentration of the dimethyl sulfide is more than 25 ppm, and/or the concentration of the dimethyl disulfide is more than 5 ppm, so that a foul odor is generated.

(Method for Evaluating Apparent Tg)

Using a thermal analysis measuring device (model "SSC/5200" manufactured by Seiko Instruments Inc.), a loss modulus (E") and a storage modulus (E') of the fibers were measured in accordance with JIS K 7244 under the conditions of a frequency of 0.05 Hz, a load of 25 mN±10 mN, and a temperature rise rate of 5° C./min. Then, the dynamic viscoelasticity (tan δ) was calculated by the following formula, and a temperature at which the dynamic viscoelasticity (tan δ) reached the maximum value was defined as a peak temperature of tan δ (apparent Tg).

Dynamic viscoelasticity(tan δ)=Loss modulus($E''$)/ Storage modulus($E'$)

TABLE 1

|  | Solvent A and its content in fibers (% by mass) | Content of epoxy group-containing compound in fibers (% by mass) | Concentration of odorous components generated (ppm) DMS | DMDS | Evaluation of foul odor | HWS properties Length of fiber bundle (mm) | Evaluation | Glass transition temperature (° C.) |
|---|---|---|---|---|---|---|---|---|
| Ex. 1 | dimethyl sulfoxide: 1.14 | 1.2 | 21 | <1 | B | 164.0 | A | 80.4 |
| Ex. 2 | dimethyl sulfoxide 1.00 | 1.2 | 18 | 1 | B | 164.0 | A | 85.3 |
| Ex. 3 | dimethyl sulfoxide: 0.71 | 1.2 | 11 | <1 | B | 171.5 | A | 86.9 |
| Ex. 4 | dimethyl sulfoxide: 0.74 | 1.2 | <1 | <1 | A | 170.5 | A | 85.0 |
| Ex. 5 | dimethyl sulfoxide: 1.13 | 0.1 | 19 | 4 | B | 162.5 | A | 83.6 |
| Ex. 6 | dimethyl sulfoxide: 1.14 | 1.2 | 7 | <1 | B | 160.0 | A | 82.6 |
| Ex. 7 | dimethyl sulfoxide: 0.27 dimethyl sulfone: 0.19 | 1 | <1 | <1 | A | 171.0 | A | 88.2 |
| Ex. 8 | dimethyl sulfoxide: 0.01 dimethyl sulfone: 0.68 | 0.7 | <1 | <1 | A | 169.5 | A | 86.3 |
| Ex. 9 | dimethyl sulfoxide: 0.01 dimethyl sulfone: 0.49 | 1.2 | <1 | <1 | A | 173.0 | A | 87.8 |
| Ex. 10 | dimethyl sulfoxide: 0.70 dimethyl sulfone: 1.10 | 4.6 | <1 | <1 | A | 158.0 | A | 81.9 |
| Ex. 11 | dimethyl sulfoxide: 0.02 ethylene carbonate: 0.45 | 1 | <1 | <1 | A | 172.8 | A | 89.0 |
| Ex. 12 | dimethyl sulfoxide: 0.02 sulfolane: 0.48 | 0.7 | <1 | <1 | A | 173.0 | A | 88.1 |
| Ex. 13 | dimethyl sulfoxide: 0.01 dimethyl sulfone: 0.70 | 1.2 | <1 | <1 | A | 170.0 | A | 86.3 |
| Comp. Ex. 1 | dimethyl sulfoxide: 0.89 | 0 | 56 | 16 | C | 170.0 | A | 85.3 |
| Comp. Ex. 2 | dimethyl sulfoxide: 0.26 | 0 | 33 | 8 | C | 178.8 | B | 89.3 |
| Comp. Ex. 3 | dimethyl sulfoxide: 0.14 | 0 | 8 | 2 | B | 200.0 | B | 94.3 |
| Comp. Ex. 4 | dimethyl sulfoxide: 0.20 | 1.0 | 3 | <1 | B | 178.5 | B | 92.7 |

As can be seen from the results in Table 1, the acrylic fibers in Examples 1 to 13, including 0.3 to 2% by mass of the solvent A and 0.1 to 5% by mass of the epoxy group-containing compound, had good curl setting properties with hot water, since the evaluation of their curl setting properties showed that the length of the fiber bundle was 175 mm or less. Moreover, the heat tests on the acrylic fibers in Examples 1 to 13 showed that the concentration of the dimethyl sulfide was 25 ppm or less and the concentration of the dimethyl disulfide was 5 ppm or less, and thus almost no malodorous components were generated. In particular, the acrylic fibers in Examples 7 to 13 included at least one selected from the group consisting of dimethyl sulfone, ethylene carbonate, and sulfolane as the solvent A. The heat tests on the acrylic fibers in Examples 7 to 13 showed that the concentrations of the dimethyl sulfide and the dimethyl disulfide were each 1 ppm or less, and thus no malodorous components were generated.

The acrylic fibers in Comparative Example 1 had good curl setting properties with hot water because the content of the dimethyl sulfoxide in the fibers was 0.3% by mass or more. However, the acrylic fibers in Comparative Example 1 did not include an epoxy group-containing compound. Therefore, the heat test showed that the concentration of the dimethyl sulfide was 56 ppm and the concentration of the dimethyl disulfide was 16 ppm, and thus malodorous components were generated. The acrylic fibers in Comparative Example 2 had poor curl setting properties with hot water because the content of the dimethyl sulfoxide in the fibers was less than 0.3% by mass. Moreover, the acrylic fibers in Comparative Example 2 did not include an epoxy group-containing compound. Therefore, the heat test showed that odorous components were generated. The acrylic fibers in Comparative Example 3 had poor curl setting properties with hot water because the content of the dimethyl sulfoxide in the fibers was less than 0.3% by mass. The acrylic fibers in Comparative Example 4 included an epoxy group-containing compound, and therefore the heat test showed that almost no odorous components were generated. However, the acrylic fibers in Comparative Example 4 had poor curl setting properties with hot water because the content of the dimethyl sulfoxide in the fibers was less than 0.3% by mass.

Although the disclosure has been described with respect to only a limited number of embodiments, those skilled in the art, having benefit of this disclosure, will appreciate that various other embodiments may be devised without departing from the scope of the present invention. Accordingly, the scope of the present invention should be limited only by the attached claims.

What is claimed is:

1. An acrylic fiber for artificial hair comprising an acrylic polymer,
   wherein the acrylic polymer comprises 29.5 to 79.5% by mass of acrylonitrile, 20 to 70% by mass of vinyl chloride and/or vinylidene chloride, and 0.5 to 5% by mass of a vinyl monomer comprising a sulfonic acid group,
   wherein the acrylic fiber for artificial hair further comprises: 0.3 to 2% by mass of a solvent for the acrylic polymer; and 0.1 to 5% by mass of a compound comprising an epoxy group, and
   wherein the compound comprising an epoxy group is one or more of the group consisting of a polymer comprising, glycidyl methacrylate, a polymer comprising glycidyl acrylate, an epoxidized vegetable oil, a glycidyl ether-type epoxy resin, a glycidyl amine-type epoxy resin, a glycidyl ester-type epoxy resin, and a cyclic aliphatic-type epoxy resin.

2. The acrylic fiber for artificial hair according to claim 1, wherein the solvent for the acrylic polymer is at least one selected from the group consisting of dimethyl sulfoxide, N,N-dimethylformamide, dimethylacetamide, dimethyl sulfone, ε-caprolactam, ethylene carbonate, and sulfolane.

3. The acrylic fiber for artificial hair according to claim 2, wherein the solvent for the acrylic polymer is dimethyl sulfone and/or dimethyl sulfoxide.

4. The acrylic fiber for artificial hair according to claim 1, wherein the compound comprising an epoxy group is the polymer comprising glycidyl methacrylate and/or the polymer comprising glycidyl acrylate.

5. The acrylic fiber for artificial hair according to claim 4, wherein the compound comprising an epoxy group is (a) a copolymer of styrene and glycidyl methacrylate; (b) polyglycidyl methacrylate; or (c) a combination thereof.

6. The acrylic fiber for artificial hair according to claim 1, wherein the acrylic fiber has an apparent glass transition temperature of 89° C. or less, which is a peak temperature of dynamic viscoelasticity (tan δ) expressed by the following formula 1:

Dynamic viscoelasticity(tan δ)=Loss modulus($E''$)/Storage modulus($E'$),   (1), where the loss modulus ($E''$) and the storage modulus ($E'$) are measured in accordance with JIS K 7244.

7. The acrylic fiber for artificial hair according to claim 1, wherein when 0.02 g of the acrylic fiber is placed in a 20 mL vial and heated at 140° C. for 5 minutes, 0 to 25 ppm of the dimethyl sulfide and 0 to 5 ppm of the dimethyl disulfide are generated from the acrylic fiber in the vial.

8. The acrylic fiber for artificial hair according to claim 7, wherein the concentration of the dimethyl sulfide is 1 ppm or less and the concentration of the dimethyl disulfide is 1 ppm or less.

9. The acrylic fiber for artificial hair according to claim 1, wherein a fiber bundle of the acrylic fiber has curl setting properties satisfying the following:
the fiber bundle with a total fineness of 4600 dtex obtained by cutting the acrylic fiber to a length of 450 mm is wound around a 15 mm diameter pipe and fixed,
the fiber bundle is immersed in hot water at 80° C. for 15 seconds, and then dried by ventilation drying at room temperature (25±5° C.) and a relative humidity of 50% for 8 hours, and
the length of the fiber bundle that is hanged immediately after removal from e pipe is 175 mm or less.

10. A method for producing an acrylic fiber for artificial hair comprising an acrylic polymer, the method comprising:
preparing a spinning solution comprising the acrylic polymer, a compound comprising an epoxy group, and a solvent for the acrylic polymer; and
wet spinning the spinning solution to form the acrylic fiber,
wherein the acrylic polymer comprises 29.5 to 79.5% by mass of acrylonitrile, 20 to 70% by mass of vinyl chloride and/or vinylidene chloride, and 0.5 to 5% by mass of a vinyl monomer comprising a sulfonic acid group,
wherein the acrylic fiber comprises: 0.3 to 2% by mass of the solvent for the acrylic polymer; and 0.1 to 5% by mass of the compound comprising an epoxy group, and
wherein the compound comprising an epoxy group is one or more of the group consisting of a polymer comprising glycidyl methacrylate, a polymer comprising glycidyl acrylate, an epoxidized vegetable oil, a glycidyl ether-type epoxy resin, a glycidyl amine-type epoxy resin, a glycidyl ester-type epoxy resin, and a cyclic aliphatic-type epoxy resin.

11. The method for producing an acrylic fiber for artificial hair according to claim 10, the method further comprising:
forming the acrylic fiber by coagulating the spinning solution,
washing the acrylic fiber by water,
applying oil and a solvent for the acrylic polymer that is the same as or different from the solvent in the spinning solution to the water-washed acrylic fiber, and
drying the acrylic fiber after e oil and the solvent are applied to the acrylic fiber.

12. The method for producing an acrylic fiber for artificial hair according to claim 10, wherein the spinning solution is prepared by dissolving the acrylic polymer in dimethyl sulfoxide, and adding the compound comprising an epoxy group to the dimethyl sulfoxide comprising the acrylic polymer.

13. The method for producing an acrylic fiber for artificial hair according to claim 11, wherein the spinning solution is prepared by obtaining an acrylic polymer solution by dissolving the acrylic polymer in dimethyl sulfoxide, and adding the compound comprising an epoxy group to the acrylic polymer solution.

14. A hair ornament product comprising an acrylic fiber for artificial hair comprising an acrylic polymer,
wherein the acrylic polymer comprises 29.5 to 79.5% by mass of acrylonitrile, 20 to 70% by mass of vinyl chloride and/or vinylidene chloride, and 0.5 to 5% by mass of a vinyl monomer comprising a sulfonic acid group,
wherein the acrylic fiber for artificial hair comprises 0.3 to 2% by mass of a solvent for the acrylic polymer and 0.1 to 5% by mass of a compound comprising an epoxy group, and
wherein the compound comprising an epoxy group is one or more of the group consisting of a polymer comprising glycidyl methacrylate, a polymer comprising glycidyl acrylate, an epoxidized vegetable oil, a glycidyl ether-type epoxy resin, a glycidyl amine-type epoxy resin, a glycidyl ester-type epoxy resin, and a cyclic aliphatic-type epoxy resin.

15. The hair ornament product according to claim 14, wherein the solvent for the acrylic polymer is at least one selected from the group consisting of dimethyl sulfoxide, N,N-dimethylformamide, dimethylacetamide, dimethyl sulfone, ε-caprolactam, ethylene carbonate, and sulfolane.

16. The hair ornament product according to claim 15, wherein the solvent for the acrylic polymer is dimethyl sulfone and/or dimethyl sulfoxide.

17. The hair ornament product according to claim 14, wherein the compound comprising an epoxy group is the polymer comprising glycidyl methacrylate and/or the polymer comprising glycidyl acrylate.

18. The hair ornament product according to claim 17, wherein the compound comprising an epoxy group is (a) a copolymer of styrene and glycidyl methacrylate; (b) polyglycidyl methacrylate; or (c) a combination thereof.

19. The hair ornament product according to claim 14, wherein the hair ornament product has an apparent glass transition temperature of 89° C. or less, which is a peak temperature of dynamic viscoelasticity (tan δ) expressed by the following formula 1:

Dynamic viscoelasticity(tan δ)=Loss modulus($E''$)/Storage modulus($E'$),   (1), where the loss modulus ($E''$) and the storage modulus ($E'$) are measured in accordance with JIS K 7244.

20. The hair ornament product according to claim 14, wherein the hair ornament product is at least one selected from the group consisting of a fiber bundle for hair, a hair weave, a wig, a braid, toupee, a hair extension, and a hair accessory.

* * * * *